(12) United States Patent
Yang et al.

(10) Patent No.: US 9,539,445 B2
(45) Date of Patent: Jan. 10, 2017

(54) TYPE OF ANION-CONTAINING CALCIUM PHOSPHATE COMPOUND FOR DENTAL REMINERALIZATION

(75) Inventors: Jen-Chang Yang, Taipei (TW); Nai-Chia Teng, Taipei (TW); Chien-Chung Chen, Taipei (TW); Sheng-Yang Lee, Taipei (TW); Chen-Feng Ma, Taipei (TW); Dian-Yu Ji, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 457 days.

(21) Appl. No.: 12/951,455

(22) Filed: Nov. 22, 2010

(65) Prior Publication Data
US 2012/0129135 A1 May 24, 2012

(51) Int. Cl.
  *A61Q 11/00* (2006.01)
  *A61K 8/24* (2006.01)
  *A61K 8/365* (2006.01)
  *A61K 8/02* (2006.01)

(52) U.S. Cl.
  CPC ............ *A61Q 11/00* (2013.01); *A61K 8/0208* (2013.01); *A61K 8/24* (2013.01); *A61K 8/365* (2013.01)

(58) Field of Classification Search
  CPC ........ A61K 8/24; A61K 8/365; A61K 8/0208; A61Q 11/00
  See application file for complete search history.

(56) References Cited

U.S. PATENT DOCUMENTS

| | | | |
|---|---|---|---|
| 4,145,282 A * | 3/1979 | Bruckenstein | 210/711 |
| 5,037,639 A | 8/1991 | Tung | |
| 5,268,167 A | 12/1993 | Tung | |
| 5,427,768 A | 6/1995 | Tung | |
| 5,437,857 A | 8/1995 | Tung | |
| 5,460,803 A | 10/1995 | Tung | |
| 5,508,342 A * | 4/1996 | Antonucci et al. | 524/788 |
| 5,858,333 A | 1/1999 | Winston et al. | |
| 2006/0134025 A1 | 6/2006 | Trivedi et al. | |
| 2006/0140884 A1 | 6/2006 | Worrell et al. | |
| 2006/0286044 A1 | 12/2006 | Robinson et al. | |
| 2008/0171001 A1 | 7/2008 | Engelman et al. | |

FOREIGN PATENT DOCUMENTS

GB 900115 * 7/1962

OTHER PUBLICATIONS

Ottolengui, R. Items of Interest. A monthly magazine of dental art. Science and Literature. New York: Consolidated Dental Manufacturing Co., 1907.*
Brečević et al. (Calcif. Tissue Int. 28, 131-136 (1979)).*
Mathew et al. (Journal of Research of the National Institute of Standards and Technology. vol. 106, No. 6, Nov.-Dec. 2001).*
Hanno zur Loye, "X-Ray Diffraction: How it works—What it can and cannot tell us". Univ. of South Carolina. 2001. Slides 1-34.*
Brečević et al. Calc. Tiss. Res. 10, 82-90 (1972).*
Lyman Kebler ("The Chemical Composition of Calcium Lacto-Phosphate", Am. J. Pharm., vol. 73, Oct. 1901. p. 499).*

* cited by examiner

*Primary Examiner* — Jeffrey S Lundgren
*Assistant Examiner* — Chris Simmons
(74) *Attorney, Agent, or Firm* — Ladas & Parry LLP

(57) ABSTRACT

The invention provides an anion-containing calcium phosphate compound, composition and dental patch comprising the same and their use in remineralizing teeth. The anion-containing calcium phosphate compound has the following formula:

$$(Ca^{+2})_x(anion^{-a})_y(PO_4^{-3})_z$$

wherein $2x=(a*y+3z)$;
a is an integer of 1 to 3; and
each of x, y and z is not 0.

14 Claims, 4 Drawing Sheets

Teeth restoration effect of CLP patches
A: 0 min   D: 2 days 23 hrs 30 min
B: 2 days  E: 2 days 23 hrs 45 min
C: 2 days

TYPE OF ANION-CONTAINING CALCIUM PHOSPHATE COMPOUND FOR DENTAL REMINERALIZATION

FIELD OF THE INVENTION

The present invention provides a new type of material for dental remineralization. Particularly, the invention provides an anion-containing calcium phosphate compound and especially its derived dental patch comprising the same and use in teeth remineralization.

BACKGROUND OF THE INVENTION

Teeth are mainly composed of enamel, dentin, and pulp chamber rich with nerves and blood vessels. Enamel and dentin are highly calcified hard tissue because they contain hydroxyapatite (HAp).

In the oral environment, the phosphates and calcium ions in the liquid phase (saliva) and the solid phase (enamel) maintain a dynamic equilibrium between demineralization and remineralization. Demineralization is the process of mineral loss from teeth caused by plaque acids or dietary acids. Demineralization can occur on tooth surfaces or below tooth surfaces depending upon the composition of the acids, concentration and pH. Demineralization may increase due to various factors affecting the balance of the equilibrium. However, inhibition of oral bacterial growth, or buffering of acidity caused by soft drinks or bacteria metabolism may aid tooth repair and prevent/alleviate caries, thereby avoiding pain and tooth loss.

Dental caries is a state of a dental carious cavity caused by the dissolution of hydroxyapatite from teeth (demineralization) which cannot naturally return to a healthy state by saliva remineralization alone. Dental decay and caries usually occur as the result of attack by acids in the mouth or saliva. A lesion or cavity in the enamel thus occurs and, if deep enough, renders the tooth vulnerable to attack by decay-producing bacteria. These acids are readily produced by fermentative catabolism of dietary carbohydrates by various plaque-forming organisms such as S. mutans. Many studies have shown that the consumption of fermentable sugars can result in plaque pH changes below the critical level (pH 5.5) at which enamel starts to dissolve.

Remineralization refers to the process of repair of acid damaged tooth structure by the recrystallization of mineral salts on the tooth architecture. Remineralization processes are a natural protective feature of saliva against the formation of tooth cavities, as saliva is supersaturated with respect to calcium phosphate tooth mineral salts. Remineralization and resistance to demineralization represent primary mechanisms toward the reduction of tooth decay or other acid insults.

In view of the dynamic equilibrium mechanism, remineralization can be improved by increasing the concentration of phosphate ions and calcium ions in the oral environment. Among various calcium phosphate salts, amorphous calcium phosphate (ACP; $K_{sp}$: $10^{-24.8}$) is a good source of calcium ions and phosphate ions because of its advantageous solubility. However, after ACP contacts with water in a physiological environment, the solubility of ACP decreases as it transforms into crystalline hydroxyapatite ($Ca_{10}(PO_4)_6(OH)_2$; $K_{sp}$: $10^{-116.8}$) through phase transformation. Furthermore, ACP only remains in mouth or dental surface for a short time, so it is difficult to fully demonstrate its effect. In 2004, Eric Reynolds of the University of Melbourne, Australia, used peptide fragments produced from enzyme-cleaved casein as carriers to chelate with ACP to form casein phosphopeptide-amorphous calcium phosphate complex (CPP-ACP) and constitute a core-shell structure to stabilize the amorphous structure of ACP and prevent ACP from transforming into crystalline calcium phosphate. This maintains the high solubility of ACP, attaches ACP to oral surfaces securely, keeps ACP for a long term efficacy in preventing caries. Although CPP-ACP is effective in preventing caries, its popularity is limited due to a potential milk protein allergy in some subjects which is triggered by casein.

Taiwan Patent Publication No. 200637587 (U.S. patent application Ser. No. 11/020,010) discloses an oral care composition comprising xylitol. Although the composition can reduce oral acidity and prevent dental caries, the composition fails to prove remineralization effect.

Taiwan Patent Publication No. 200637605 (U.S. patent application Ser. No. 11/256,861) discloses a toothpaste composition comprising a wetting agent, an abrasive, and an antibacterial component including ursolic acid and carnosic acid. The application relates to an anti-bacteria formulation that is irrelevant to remineralization.

Taiwan Patent Publication No. 200640531 (U.S. patent application Ser. No. 11/256,788) discloses an oral care composition comprising oregano for inhibiting bacteria and preventing dental plaque, inflammation and oxidation. However, the composition fails to provide a remineralization effect.

U.S. Pat. Nos. 5,037,639, 5,268,167, 5,437,857, 5,427,768 and 5,460,803 involve various amorphous calcium phosphate compounds (such as amorphous calcium phosphate (ACP), amorphous calcium phosphate fluoride (ACPF) and amorphous calcium carbonate phosphate (ACCP)) for remineralization. However, these compounds are intended for crystallization after contact with water, so they are not suitable for commercialization.

U.S. Pat. No. 5,858,333 provides a two-part oral product capable of remineralizing subsurface lesions and/or mineralizing exposed dentinal tubules in teeth which is composed of cationic and anionic discrete parts. The cationic discrete part contains ACP. However, the ACP in the product cannot stay in continuous contact with teeth for a long time, so its remineralization effect is not satisfactory.

U.S. Patent Application No. 20080171001 provides new toothpaste comprising casein phosphopeptide amorphous calcium phosphate and its remineralization effect is also not satisfactory. Taiwan Patent Application No. 200637587 uses calcium glycerophosphate for teeth remineralization. However, the calcium bonds to glycerophosphate in the calcium glycerophosphate but not glycerol and phosphate separately, and the solubility of the calcium glycerophosphate is relatively low.

Therefore, there is still a need to develop a material with advantageous remineralization effect.

SUMMARY OF THE INVENTION

One object of the invention is to provide an anion-containing calcium phosphate compound having the following formula:

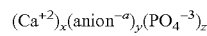

wherein $2x=(a*y+3z)$;
a is an integer of 1 to 3; and each of x, y and z is not 0.

Another object of the invention is to provide a dental care composition comprising the anion-containing calcium phosphate compound of the invention and an additional orally acceptable carrier.

A further object of the invention is to provide a patch for tooth remineralization having a tooth-adhering layer comprising the anion-containing calcium phosphate compound or composition of the invention and a backing layer.

DETAILED DESCRIPTION OF THE INVENTION

Figure 1:
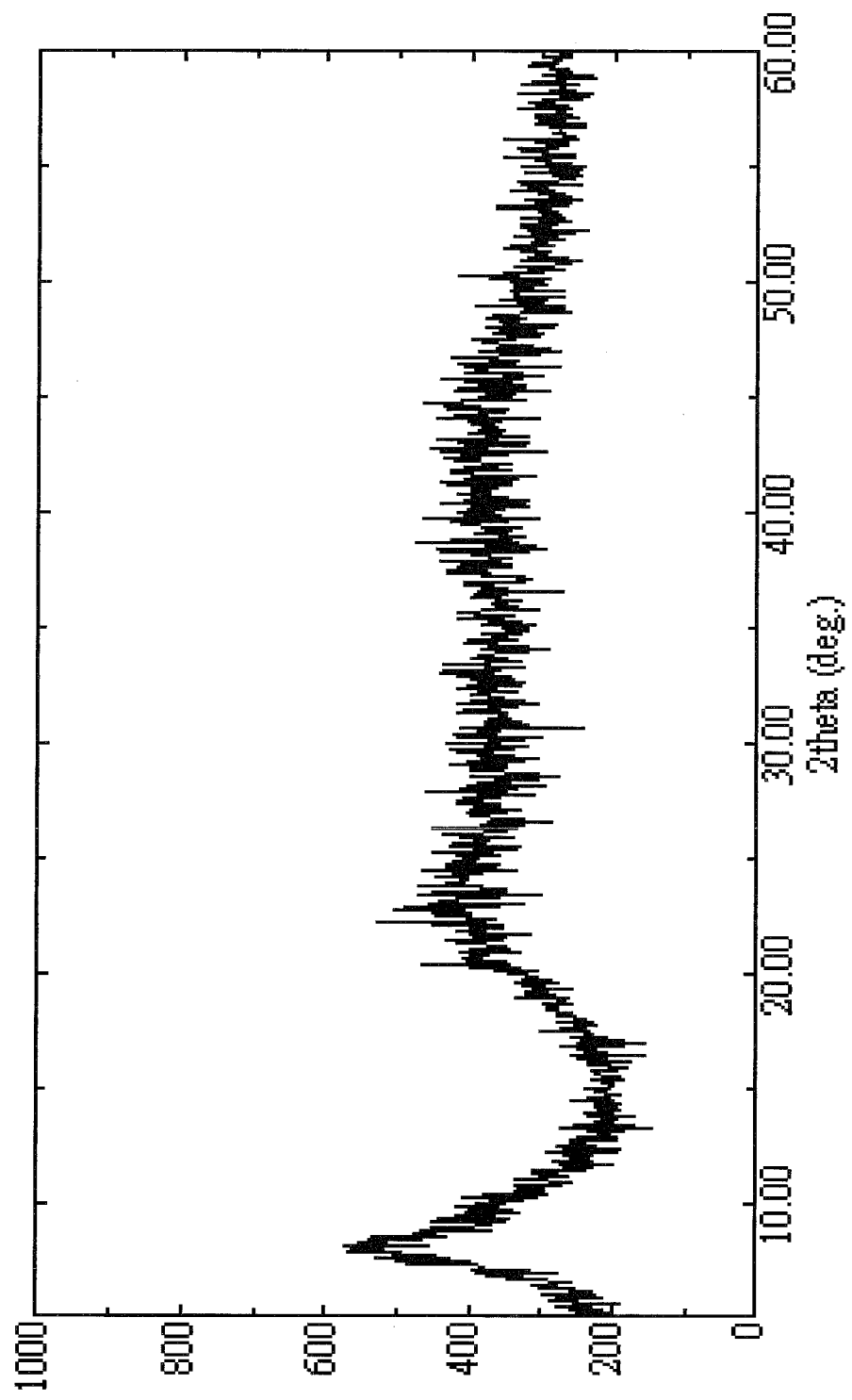
FIG. 1 shows X-ray powder diffractogram (XRPD) of the calcium lactate phosphate cluster of the invention.

The invention discovers an anion-containing calcium phosphate compound with a new type of molecular structure. It is unexpected that the anion-containing calcium phosphate compound of the invention has poor crystallinity but high solubility and stability, so it can improve remineralization to seal dentinal tubules and recovery of lesions in teeth.

In one aspect, the invention provides an anion-containing calcium phosphate compound having the following formula:

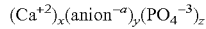

$$(Ca^{+2})_x(anion^{-a})_y(PO_4^{-3})_z$$

wherein $2x = (a*y + 3z)$;
a is an integer of 1 to 3; and
each of x, y and z is not 0.

Herein, "comprising" means that other steps and other ingredients which do not affect the end result can be added. This term encompasses the terms "consisting of" and "consisting essentially of".

"Dental care composition" refers to a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity. The dental care composition of the present invention may be in the form of a toothpaste, dentifrice, tooth powder, mousse, topical oral gel, mouth rinse, denture product, mouth spray, lozenge, oral tablet, troche, dental patch or chewing gum.

The term "teeth" as used herein refer to natural teeth as well as artificial teeth or dental prosthesis.

The term "orally acceptable carrier" as used herein means any safe and effective materials for use in the compositions of the present invention. Such materials include fluoride ion sources; anticalculus agents; additional remineralizing agents such as calcium ion sources, phosphate ion sources and strontium ion sources; buffers; abrasive polishing materials; teeth whitening or bleaching agents such as peroxide sources; alkali metal bicarbonate salts; thickening materials; humectants; water; surfactants; titanium dioxide; flavor system; sweetening agents; xylitol; coloring agents; and mixtures thereof.

The terms "mineralization" and "remineralization" are used interchangeably and refer to crystallization of mineral salts in the tooth architecture.

According to the invention, the "anion-containing calcium phosphate compound" is a complex having a unit containing calcium phosphate in the core and calcium-anion surrounding the calcium phosphate so that the calcium, anion and phosphate form the formula: $(Ca^{+2})_x(anion^{-a})_y(PO_4^{-3})_z$, wherein $2x=(a*y+3z)$, "a" is an integer of 1 to 3, and each of x, y and z is not 0. In addition, the symbol "*" means multiplication. The binding between the calcium phosphate and anions depends on ion-ion bonding. Due to the anion binding into the calcium phosphate structure, the anion-containing calcium phosphate compound has poor crystallinity but high solubility and stability in aqueous environment than calcium phosphate and will not transform to crystalline structure.

The above-mentioned structure makes the anion-containing calcium phosphate compound of the invention have poor crystallinity. However, this compound has high solubility and stability in aqueous solution, so the release of calcium ion is increased to achieve an improved remineralization effect and recovery of lesions in teeth.

The anion-containing calcium phosphate compound of the invention is prepared by providing a calcium ion solution, an anion solution and a phosphate anion solution; mixing the three solution to form the anion-containing calcium phosphate compound; and removing precipitates. According to the invention, the preparation of the anion-containing calcium phosphate compound may further include a drying step.

According to the invention, the source of the calcium ions and the source of the phosphate ions can be a single compound, a mixture of single compounds, or separate compounds. The calcium ions may be from any inorganic calcium compound or organic calcium compound and the phosphate anions may be from any phosphate compounds. Suitable single sources of calcium and phosphate ions include, but are not limited to, dicalcium phosphate anhydrous, tetracalcium phosphate, dicalcium phosphate dihydrate, tricalcium phosphate, and mixtures thereof. Suitable separate sources of the calcium ions and phosphate ions are, for example, calcium chloride, calcium sulfate, calcium aluminosilicate, calcium carbonate, calcium chloride, calcium ascorbate, calcium oxide, calcium hydroxide, calcium lactate, calcium citrate or calcium gluconate as calcium ion source and sodium phosphate or potassium phosphate as phosphate ion source.

According to the invention, the source of an anion is any halides, inorganic acids or organic acids. Preferably, the source of the anion is an organic acid. Suitable inorganic acids include, but not limited to, nitrate, sulfate, halide, and carbonate. Suitable organic acids include, but not limited to, lactate, citrate, acetate, tartrate, maleate, succinate, pyruvate, glycolate, glutarate, malonate and phthalate.

The preferred embodiments of the anion-containing calcium phosphate compound include, but not limited to, calcium lactate phosphate, calcium citrate phosphate, calcium sulfate phosphate and calcium maleate phosphate. Most preferably, the anion-containing calcium phosphate compound is calcium lactate phosphate that has the formula: $Ca_9L_{12}P_2$ and Ca/P ratio of about 4.5. The calcium lactate phosphate forms an octahedral structure wherein tricalcium phosphate is located in the center of the structure and lactate-calcium-lactate is located on the vertexes of the structure. As mentioned above, the anion-containing calcium phosphate compound has an increased solubility. For example, the solubility of the materials known in the art for dental remineralization, calcium glycerophosphate and calcium lactophosphate, are 2 g/100 ml water and 0.3-1 g/100 ml water, whereas the solubility of calcium lactate phosphate is 3.1 to 11.1 g/100 ml water.

In another aspect, the invention provides a dental care composition comprising the anion-containing calcium phosphate compound of the invention and an additional orally acceptable carrier.

In preparing the present compositions, it is desirable to add one or more aqueous carriers to the compositions. Such materials are well known in the art and are readily chosen by one skilled in the art on the basis of the physical and aesthetic properties desired for the compositions being prepared. These carriers may be included at levels which do not interfere with or prohibit the effects of the anion-containing calcium phosphate compound of the invention. Aqueous carriers typically constitute about 50% to about 99%, preferably from about 70% to about 98%, and more preferably from about 80% to about 95%, by weight of the oral care composition.

The present compositions may contain a buffering agent. Buffering agents, as used herein, refer to agents that can be used to adjust the pH of the compositions to a range of about pH 4 to about pH 10. The dental care composition containing a polymeric mineral surface active agent will typically have a slurry pH of about 4 to about 10, preferably about 4.5 to about 8, and more preferably about 5.5 to about 7. The buffering agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. Buffering agents are used at a level of about 0.1% to about 55%, preferably from about 1% to about 30% or about 1% to about 10%, and more preferably from about 1.5% to about 3%, by weight of the present composition.

The present compositions may optionally contain anticalculus agents such as calcium lactate, calcium lactophosphate, double salts of calcium lactate and mixtures thereof, pyrophosphates and other polyphosphates. Pyrophosphates are among the best known for use in dental care products. Pyrophosphate salts may be used in the present invention as anticalculus agents or as buffering agents. The pyrophosphate salts useful in the present compositions include dialkali metal pyrophosphate salts, tetra alkali metal pyrophosphate salts, and mixtures thereof. Disodium dihydrogen pyrophosphate, tetrasodium pyrophosphate, and tetrapotassium pyrophosphate in their unhydrated as well as hydrated forms are the preferred species. Additional anticalculus agents that may be used in place of or in combination with the pyrophosphate salts include such known materials as synthetic anionic polymers.

An abrasive polishing material may also be included in the dental care compositions. The abrasive polishing material contemplated for use in the compositions of the present invention can be any material which does not excessively abrade dentin. The abrasive polishing material should be formulated in the dental care composition in such a way that it does not compromise the stability of any ingredients, in particular the fluoride ion source and the polyphosphonate containing polymeric agent. Typical abrasive polishing materials include silica gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, resinous abrasive materials such as particulate condensation products of urea and formaldehyde, and others such as those disclosed in U.S. Pat. No. 3,070,510. Mixtures of abrasives may also be used.

The present composition may include a teeth whitening or bleaching agent. The actives suitable for whitening are selected from the group consisting of peroxides, metal chlorites, perborates, percarbonates, peroxyacids, persulfates, and combinations thereof. Suitable peroxide compounds include hydrogen peroxide, urea peroxide, calcium peroxide, carbamide peroxide, and mixtures thereof. A preferred peroxide source is calcium peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. A preferred chlorite is sodium chlorite. A preferred percarbonate is sodium percarbonate. Preferred persulfates are oxones. The present composition may contain about 0.01% to about 10%, preferably about 0.1% to about 5%, more preferably about 0.2% to about 3%, and most preferably about 0.3% to about 0.8% of a teeth whitening active by weight of the present composition.

The present invention provides compositions in the form of toothpastes, dentifrices, tooth powder, topical oral gels, mouth rinses, denture product, mouth sprays, lozenges, chewable oral tablets, and chewing gums. Typically these compositions will contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an amount of about 0.1% to about 15% by weight of the present composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof.

Various other materials may be incorporated in the composition of the invention. Examples thereof are coloring or whitening agents, preservatives, silicones, chlorophyll compounds and ammoniated materials such as urea, diammoniumphosphate and mixtures thereof. These adjuvants are incorporated in the compositions in amounts which do not substantially adversely affect the properties and characteristics, and such amounts are suitably selected depending upon the particular type of preparation involved.

For some purposes it may be desirable to include antibacterial agents in the compositions of the present invention.

Any suitable flavoring or sweetening materials may be employed in formulating a flavor for the compositions of the present invention. Examples of suitable flavoring constituents include flavoring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitable flavoring and sweetening agents may together constitute about 0.01 to 5% or more of the composition.

The anion-containing calcium phosphate compound or composition of the invention can be applied in, but not limited to, toothpaste, toothpowder, dentifrice, mouth rinse, mousse, denture product, topical oral gel, oral tablet, lozenge, troche, chewing gum and dental patch.

In one embodiment, the anion-containing calcium phosphate compound or composition of the invention can be applied in tooth patch for remineralization. According to one embodiment of the invention, the patch for tooth remineralization comprises a tooth-adhering layer comprising the anion-containing calcium phosphate compound or composition of the invention and a backing layer. In another embodiment of the invention, the patch can further comprise one or more layers comprising one or more dentally active ingredient. Persons skilled in the art can determine the numbers of layers in accordance with the applications of the patch. The said tooth-adhering layer releases calcium ions and phosphate anions upon adherence to the teeth surfaces and it has a hydrophilic property and better adhesive strength. According to embodiments of the invention, in addition to anion-containing calcium phosphate compound or composition of the invention, the said tooth-adhering layer comprises one or more dentally active ingredient.

According to the invention, the backing layer is known in the art and it comprises a water-insoluble material. Examples of the water-insoluble material include, but are not limited to, light resistance paper, cellulose acetate phthalate, polyvinyl acetate, ethyl cellulose, polymethyl methacrylate, methacryloylethyl betain/methacrylate copolymer that is commercially available under the trade name of Yukaformer manufactured by Mitsubishi, methacrylic acid copolymers such as Eudragit L 100, Eudragit L 125, Eudragit L 100-55, Eudragit L 30D-55, aminoalkylmethacrylate copolymers such as Eudragit E 100, Eudragit E 125, Eudragit RL 100, Eudragit RL 30D), or mixtures thereof.

In addition to the anion-containing calcium phosphate compound or composition of the invention, the tooth-adhering layer of the patch may contain a hydrophilic polymer. According to the invention, the polymer may be, but is not limited to, polyalkylvinyl ether-maleic acid copolymer (PVM/MA copolymer) such as Gantrez AN 119, AN 139 and S-97, polyvinyl alcohol, polyacrylic acid, Poloxamer 407 (Pluronic), Pluronic F127, polyvinyl pyrrolidone-vinyl acetate copolymer (PVP/VA copolymer) such as Luviskol VA and Plasdone S PVP/VA, polyethylene oxide (Polyox), polyvinyl pyrrolidone (PVP, K-15.about.K-120), Polyquaterium-11 (Gafquat 755N), Polyquaterium-39 (Merquat plus 3330), carboxypolymethylene (Carbopol), hydroxypropylmethyl cellulose, hydroxyethyl cellulose, hydroxypropyl cellulose, gel, gelatin and alginate salt such as sodium alginate. The above-described polymers can be used alone or in combinations. Polyvinyl pyrrolidone (PVP) is the most preferred hydrophilic polymer. Solvents for these polymers include water, ethanol or mixtures thereof. Further, other organic solvents such as ethyl acetate, methylene chloride, isopropyl alcohol, acetonitrile or mixtures thereof in varied ratios may also be used as a solvent.

The patch to be attached onto teeth should be flexible enough to be deformable so that it conforms to contours of teeth. Since some polymers have a poor flexibility, suitable plasticizers may be added. Polypropylene glycol, glycerin, and polyethylene glycol are generally used as the plasticizers.

The patch of the invention may further comprise a whitening agent to whiten teeth, fluoride ion to prevent tooth decay, or a stannous ion to reduce gingivitis or plaque.

The patch of the invention may still further comprise a pigment with various colors, a flavoring agent, a sweetening agent and a moistening agent. The pigment is used to make the teeth whiter, and selected from the group consisting of titanium dioxide, talc, hydroxyapatite, zinc oxide and mixtures thereof. Examples of the flavoring agent include peppermint, spearmint, wintergreen, sage, eucalyptus oil, methylsalicylate and other fruit extracts. Examples of the sweetening agent and moistening agent include mannitol, xylitol, lactose, aspartame, and saccharin sodium.

EXAMPLE

Example 1

Preparation of Calcium Lactate Phosphate with High Solubility 0.85 g of calcium oxide (CaO), 2.81 g of lactic acid, and 0.12 g of phosphoric acid were mixed in 96.22 g of deionized water. The resulting mixture was filtrated and dried to form calcium lactate phosphate compound powder. Due to the addition of lactate, the calcium lactate phosphate compound has an irregular molecular structure with low crystallization and high solubility. In addition, calcium lactate phosphate compound is stable in water, so phase transition will not occur. As a consequence, calcium ion and phosphate ion can be released from the calcium lactate phosphate compound so that effective dental remineralization can be maintained and improved. The structure of the calcium lactate phosphate compound was determined by X-ray diffraction (XRD) and its XRD diffractogram is shown in FIG. 1. The solubility of the calcium lactate phosphate compound is 3.1-11.1 g/100 ml $H_2O$.

Example 2

Remineralization Patch of the Invention and Remineralization Assay

The patch of the invention includes a tooth-ashering layer and a backing layer. The tooth-ashering layer of the patch comprises 1.5 wt % of poly-γ-glutamic acid (γ-PGA), 2.5 wt % of glycerol, 3 wt % of calcium lactate phosphate compound of the invention, 10 wt % of polyvinylpyrrolidone (PVP) and 83 wt % of deionized water. The backing layer of the patch comprises 20 wt % of ethyl cellulose, 10 wt % of glycerol and 70 wt % of ethanol.

Figure 2:
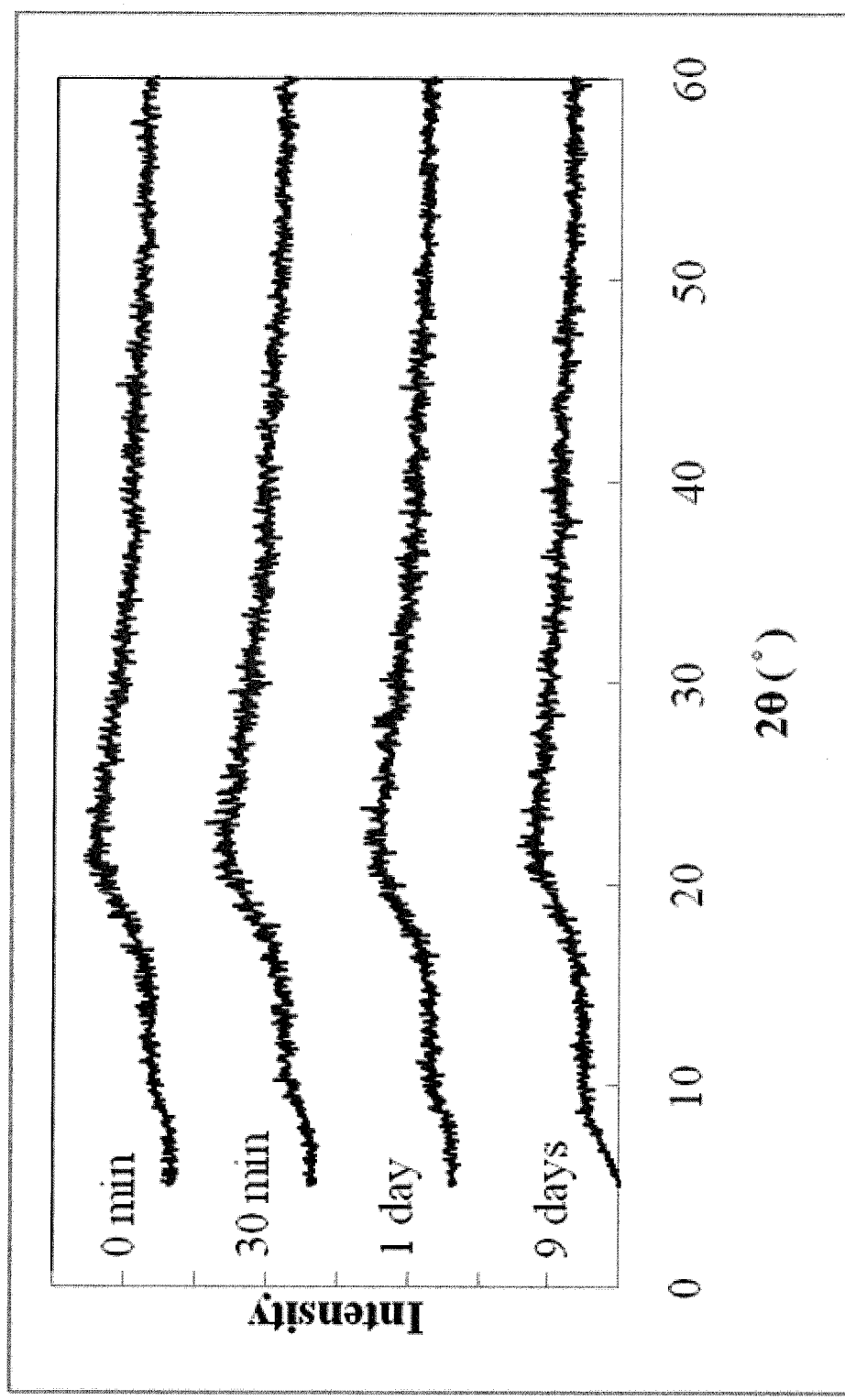
FIG. 2 shows the XRPD profiles of calcium lactate phosphate cluster placed a simulated oral environment after 0 minute, 30 minutes, 1 day and 9 days.

The remineralization patch of the invention was placed at a simulated oral environment of 37° C. and 100% humidity to evaluate whether the calcium lactate phosphate cluster in the patch was stable in a warm and humid oral environment. As shown in the XRD diffractograms of FIG. 2, the XRD profiles of calcium lactate phosphate cluster at 0 minute, 30 minutes, 1 day and 9 days remain the same, so phase transition did not occur in the calcium lactate phosphate cluster. The patch can maintain advantageous stability during usage.

The patches of the invention containing 2 wt % and 3 wt % calcium lactate phosphate, deionized water as blank, artificial saliva as positive control and amorphous calcium phosphate (ACP)/water (W) and γ-polyglutamic acid (γ-PGA)-ACP/water (W) as comparative examples were used to evaluate the remineralization effect of the patches. The effectiveness of the remineralization patch was conducted by using 1M acetic acid to etch a tooth surface for 3 minutes, attaching the patch to the tooth for remineralization and then measuring the Knoop microhardness (Knoop hardness number, KHN) of the tooth with a microhardness tester. The remineralization was measured with percentage microhardness recovery of teeth:

$$\text{Microhardness recovery}(\%) = \frac{\left(\begin{array}{c}\text{KHN of } teeth after \text{ remineralization}-\\ \text{KHN of } teeth after \text{ acid erosion}\end{array}\right)}{\left(\begin{array}{c}\text{KHN of } original teeth-\\ \text{KHN of } teeth after \text{ acid erosion}\end{array}\right)} \times 100$$

Dental remineralization occurred within 15 to 30 minutes after the patches were used. The treatment time-dependence of microhardness recovery (%) are shown in below table:

|  | Deionized water | Artificial saliva | 2% CLP patch | 3% CLP patch | ACP/W | γ-PGA-ACP/W |
|---|---|---|---|---|---|---|
| 0 min | 0.0 | 0.0 | 0.0 | 0.0 | 0.0 | 0.0 |
| 15 min | 24.7 | 7.9 | 16.6 | 57.5 | 3.4 | 7.2 |
| 30 min | 23.7 | 10.6 | 37.7 | 66.2 | 0.6 | 10.1 |
| 3 days | 17.3 | 23.1 | 45.1 | 78.7 | 13.0 | 51.9 |

Figure 3:
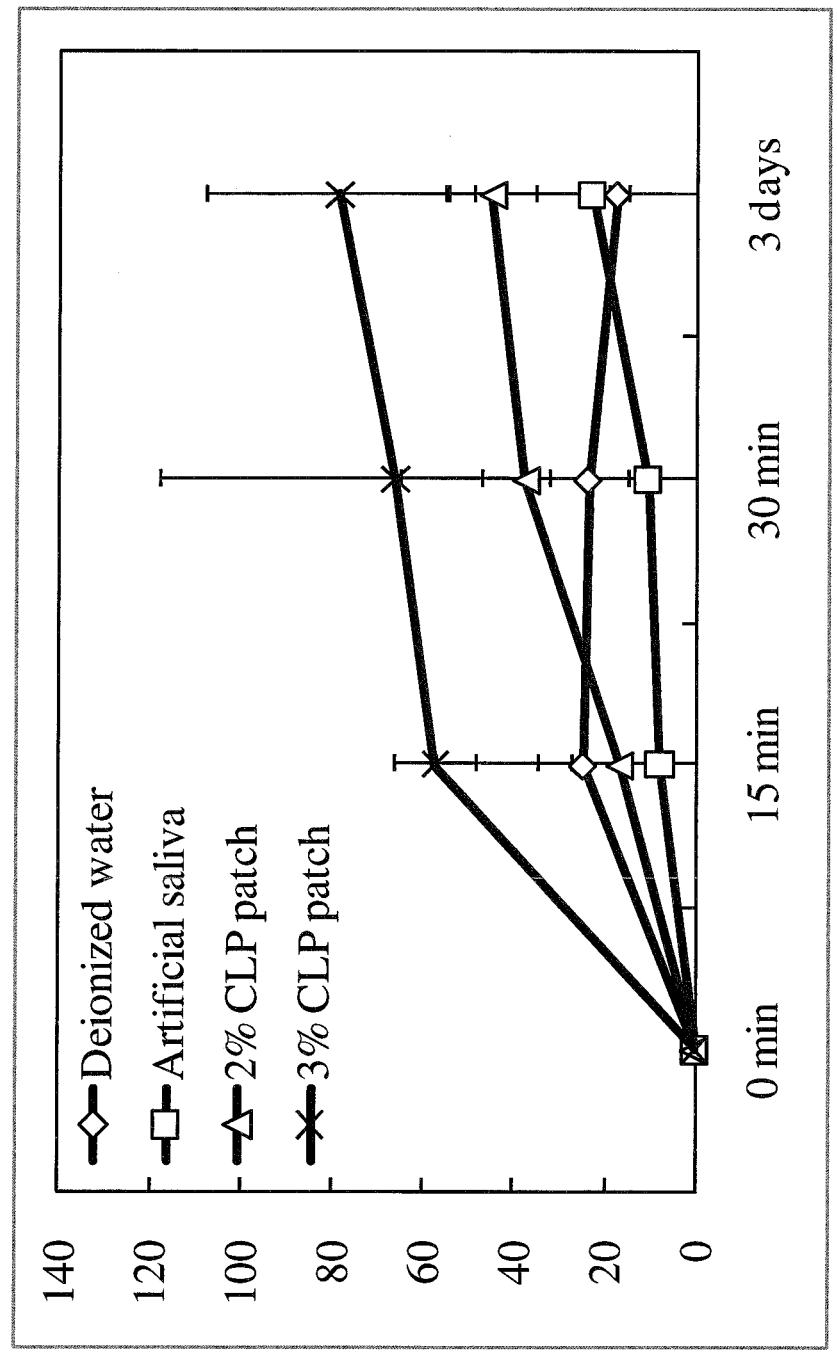
FIG. 3 shows the treatment time-dependence of hardness recovery percentage (%) of CLP patches wherein the symbol "◇" represents deionized water, the symbol "□" represents artificial saliva, the symbol "Δ" represents 2% CLP patch and the symbol "×" represents 3% CLP patch.
Figure 4:
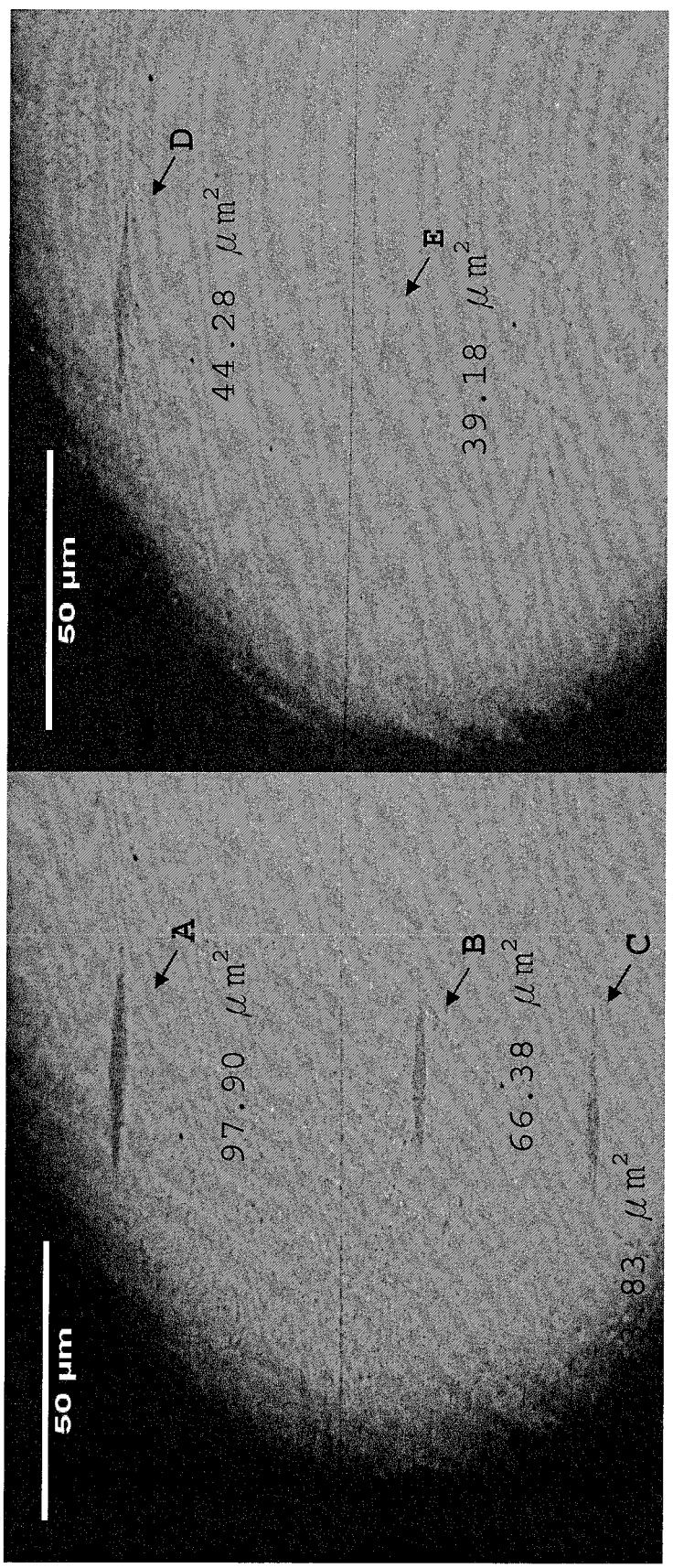
FIG. 4 shows the microscopic diagrams regarding recovery of lesions in the tooth after treatment with the patches of the invention.

The results of the above table are shown in FIG. 3. As shown in FIG. 3, the patch having 2% CLP or 3% CLP provides advantageous remineralization. The tooth after treating with the patches of the invention at 0 minute, 2 days, 2 days 23 hours 30 minutes and 2 days 23 hours 45 minutes were examined under microscope. As shown in FIG. 4, the lesion marks in the tooth were getting smaller and smaller over time. The result suggested that the patch of the invention has effect in restoring teeth.

Example 3

Solubility and Remineralization Assay of Other High Solubility Complexes of the Invention Calcium carbonate, calcium sulfate, calcium hydroxide or calcium citrate, citric acid, acetic acid, lactic acid or maleic acid and phosphate were used to form the calcium anion phosphate complex powder and the solubility of the calcium lactate phosphate complex was determined according the method mentioned in Example 1. The resulting solubility of the complexes were higher than 3.0 g/100 ml H$_2$O. In the remineralization assay, the calcium anion phosphate complexes were prepared as patches and the microhardness recovery percentages of the resulting patches were determined according to the process of Example 2. The resulting hardness recovery percentages of the patches were higher than 50%, 60% and 70% after 15 minutes, 30 minutes and 3 days, respectively.

What is claimed is:

1. A non-crystalline anion-containing calcium phosphate complex which is calcium lactate phosphate complex with the formula:
   Ca$_9^{2+}$(CH$_3$CHOHCOO$^-$)$_{12}$(PO$_4^{3-}$)$_2$ wherein the calcium lactate phosphate complex has a unit containing calcium phosphate in a core and calcium lactate surrounding the unit containing calcium phosphate surrounding the calcium phosphate,
   wherein binding between the calcium phosphate and lactate anions depends on ion-ion bonding.

2. The non-crystalline anion-containing calcium phosphate complex of claim 1, wherein the calcium and phosphate are a single source selected from the group consisting of dicalcium phosphate anhydrous, tetracalcium phosphate, dicalcium phosphate dihydrate, tricalcium phosphate, and mixtures thereof.

3. The non-crystalline anion-containing calcium phosphate complex of claim 1, wherein the source of the calcium ions is selected from the group consisting of calcium chloride, calcium sulfate, calcium aluminosilicate, calcium carbonate, calcium chloride, calcium ascorbate, calcium oxide, calcium hydroxide, calcium lactate, calcium citrate and calcium gluconate and the source of the phosphate anions is selected from the group consisting of sodium phosphate and potassium phosphate.

4. The non-crystalline anion-containing calcium phosphate complex of claim 1, wherein the source of the lactate anions is lactic acid.

5. The non-crystalline anion-containing calcium phosphate complex of claim 1, which is capable of being applied in toothpaste, toothpowder, dentifrice, mouth rinse, mousse, denture product, topical oral gel, oral tablet, lozenge, troche, chewing gum and dental patch.

6. A dental care composition comprising the anion-containing calcium phosphate complex according to claim 1 and an additional orally acceptable carrier.

7. The dental composition of claim 6, which can be applied in toothpaste, toothpowder, dentifrice, mouth rinse, mousse, denture product, topical oral gel, oral tablet, lozenge, troche, chewing gum and dental patch.

8. A patch for tooth remineralization, which comprises a tooth-adhering layer comprising the anion-containing calcium phosphate complex according to claim 1 or dental care composition according to claim 6 and a backing layer.

9. The patch of claim 8, wherein the backing layer is composed essentially of a water-insoluble material selected from the group consisting of light resistance paper, cellulose acetate phthalate, polyvinyl acetate, ethyl cellulose, polymethyl methacrylate, methacryloylethyl betain/methacrylate copolymer, methacryloyl ethyl betain/acrylate copolymer, methacrylic acid copolymer, aminoalkylmethacrylate copolymer, or mixtures thereof.

10. The patch of claim 8, wherein the tooth-adhering layer contains a hydrophilic polymer.

11. The patch of claim 10, wherein the hydrophilic polymer is selected from the group consisting of polyalkylvinyl ether-maleic acid copolymer, polyvinyl alcohol, polyacrylic acid, Poloxamer 407 (Pluronic), polyvinyl pyrrolidone-vinyl acetate copolymer, polyethylene oxide (Polyox), polyvinyl pyrrolidone (PVP), Polyquaterium-11, Polyquaterium-39, carboxypolymethylene (Carbopol), hydroxypropylmethyl cellulose, hydroxyethyl cellulose, hydroxypropyl cellulose, gelatin and alginate salt.

12. The patch of claim 10, wherein the hydrophilic polymer is PVP.

13. The patch of claim 8, wherein the tooth-adhering layer further comprises one or more dentally active ingredient.

14. The patch of claim 8, further comprising one or more layers comprising dentally active agents.

* * * * *